United States Patent [19]

Kuroda et al.

[11] Patent Number: 4,933,293
[45] Date of Patent: Jun. 12, 1990

[54] METHOD OF CLASSIFYING LEUKOCYTES BY FLOW CYTOMETRY AND REAGENTS USED IN THE METHOD

[75] Inventors: Tomoyuki Kuroda; Takashi Sakata, both of Kakogawa, Japan

[73] Assignee: TOA Medical Electronics Co., Ltd., Kobe, Japan

[21] Appl. No.: 423,496

[22] Filed: Oct. 12, 1989

Related U.S. Application Data

[63] Continuation of Ser. No. 91,654, Sep. 1, 1987, abandoned.

[30] Foreign Application Priority Data

Sep. 10, 1986 [JP] Japan .................. 61-213715

[51] Int. Cl.$^5$ .......................... G01N 33/48
[52] U.S. Cl. .......................... 436/63; 424/3; 250/461.2; 356/39
[58] Field of Search .................. 436/8, 10, 63, 805; 435/2; 424/3; 250/461.2; 356/39

[56] References Cited

U.S. PATENT DOCUMENTS

| | | | |
|---|---|---|---|
| 3,619,205 | 10/1975 | Kleinerman | 356/36 |
| 3,684,377 | 8/1972 | Adams et al. | 356/36 |
| 3,883,247 | 5/1975 | Adams | 356/36 |
| 4,146,604 | 3/1979 | Kleinerman | 424/3 |
| 4,156,570 | 5/1979 | Wardlew | 356/36 |
| 4,284,412 | 8/1981 | Hansen et al. | 356/39 |
| 4,492,785 | 1/1985 | Hoffman et al. | 436/63 |
| 4,581,223 | 4/1986 | Kass | 424/3 |
| 4,596,035 | 6/1986 | Gershman et al. | 356/39 |
| 4,662,742 | 5/1987 | Chupp | 356/39 |

FOREIGN PATENT DOCUMENTS

| | | |
|---|---|---|
| 0106339 | 10/1983 | European Pat. Off. . |
| 59-853 | 1/1984 | Japan . |
| 5020820 | 3/1985 | Japan . |
| 8505684 | 12/1985 | World Int. Prop. O. . |

OTHER PUBLICATIONS

Kamentsky, Blood Cells, 6, 121–140, (1980).
Shapiro et al., J. Histochem. Cytochem. 24, 396–411, (1976).
Shapiro, J. Histochem. Cytochem., 25, 976–989, (1977).

Primary Examiner—Barry S. Richman
Assistant Examiner—T. J. Wallen
Attorney, Agent, or Firm—Fitch, Even, Tabin & Flannery

[57] ABSTRACT

A method for classifying leukocytes with a flow cytometer by means of optical measurements on fluorochrome-stained blood cells is useful in the practice of clinical testing.

7 Claims, 8 Drawing Sheets

RELATIVE INTENSITY OF
RIGHT-ANGLE SCATTERED LIGHT

LEUKOCYTE CLASSIFICATION WITH FLUORESCEIN

LEUKOCYTE CLASSIFICATION WITH DiO C5(6)

LEUCOCYTE CLASSIFICATION WITH BRILLIANT PHOSPHINE

LEUCOCYTE CLASSIFICATION WITH NEUTRAL RED

LEUCOCYTE CLASSIFICATION WITH AURAMINE O

LEUCOCYTE CLASSIFICATION WITH ASTRAZON ORANGE G

LEUCOCYTE CLASSIFICATION WITH
ASTRAZON ORANGE G AND NEUTRAL RED

LEUCOCYTE CLASSIFICATION WITH TA-2

LEUCOCYTE CLASSIFICATION WITH THREE DYES

METHOD OF CLASSIFYING LEUKOCYTES BY FLOW CYTOMETRY AND REAGENTS USED IN THE METHOD

This application is a continuation of application Ser. No. 091,654 filed Sept. 1, 1987, now abandoned.

FIELD OF THE INVENTION

The present invention relates to a method for classifying leukocytes in the practice of clinical testing and, more particularly, to a method for classifying leukocytes with a flow cytometer by means of optical measurements on fluorochrome-stained blood cells.

Leukocytes in the peripheral blood of normal subjects can be classified as being of five types consisting of lymphocytes, monocytes, neutrophils, eosinophils, and basophils. Different leukocyte types have different functions and counting of leukocytes in the blood according to their type will provide valuable information for diagnostic purposes. For instance, an increase in the number of neutrophils is associated with such diseases as inflammations, myocardial infarction and leukemia, and a decrease in their number is associated with viral diseases, hypoplastic anemia, agranulocytosis, etc. On the other hand, an increase in the number of eosinophils is found in such diseases as parasitosis, Hodgkin's disease and allergosis. An increased number of monocytes occurs either during the convalescence period of patients suffering from infectious diseases or in such diseases as monocytic leukemia.

BACKGROUND OF THE INVENTION

Classification and counting of leukocytes nave been made most commonly by the differential counting method which is also referred to as the visual counting method or simply as the manual method. In this method, a blood sample is spread on a glass slide and the blood corpuscles in the smear are fixed and stained for examination by microscopy. The technician identifies the type of individual leukocytes according to their morphological features (e.g., their size, the morphology of their nucleus and cytoplasm, and the presence or absence of granules) or the degree of dye uptake and performs classification and counting of them. At ordinary laboratories, 100-200 leukocytes are usually counted for each sample and the percentage of the total leukocyte count occupied by each type of corpuscle is recorded as a measured value.

The differential counting method has several disadvantages. First, microscopic observation must be preceded by cumbersome procedures for preparing a specimen that involve such steps as smearing a blood sample on a glass slide, fixing the corpuscles and staining them. Secondly, it is a great burden for the technician to identify subtle differences between corpuscles by microscopic classification and counting. Thirdly, it is difficult even for a skilled technician to yield consistent counts by the manual method since aside from the small number of leukocytes computed, the smeared sample often has an uneven distribution of blood corpuscles.

Various methods have been proposed for eliminating these disadvantages of the manual method of leukocyte classification by achieving automation and such automated techniques may be roughly divided into two types. The first method consists of recording the images of corpuscles with a video camera or some other suitable imaging device and classifying the leukocytes by means of image processing on a computer. The operating principle of this method is similar to that of the conventional visual counting method but primarily due to the existence of many corpuscles that defy classification by processing with a computer, this method has not yet become an ideal alternative to the manual method. Furthermore, this method is not economically feasible since it requires sophisticated equipment which is large and costly.

The other approach toward automatic classification and counting of leukocytes is based on a flow system. In this method, a blood sample having corpuscles suspended in a diluent is permitted to flow in such a way that the corpuscles will individually (one by one) pass through a narrowed detecting area and leukocyte classification is made by analyzing the signal generated by the detector. This second method of leukocyte counting which makes use of a flow system is further subdivided into two categories.

In a method of the first category, an electrolyte in which all red cells that were present have been destroyed with a lysing agent so that only leukocytes will be suspended is permitted to flow through an orifice and the change in electrical impedance that occurs at the orifice when each corpuscle passes through it is detected, with the magnitude of the detected signal being used as a basis for classification of leukocytes.

A method of the second category is characterized by the use of a flow cytometer that comprises a light source, a flow cell that permits the blood cells in a sample to flow one by one through a constricted channel, a photometric unit that detects light issuing from each blood cell, and an analyzer for analyzing the detected signals. In this method, the corpuscles in the sample which are stained are illuminated under light and the fluorescence emitted from the irradiated corpuscles is detected, optionally together with scattered light, with leukocyte classification being made in accordance with the intensity of the detected signals.

Techniques that fall within the category of this flow cytometric method are described, for example, in Japanese Patent Publication No. 853/1984 and L. A. Kamentsky, Blood Cells, 6, 121-140 (1980). According to these techniques, a blood sample is stained with 10 volumes of an acridine orange solution, incubated for 1 minute, and irradiated under a light source such as an argon ion laser. The green fluorescence and red fluorescence that are emitted from the individual corpuscles are measured and classification and counting of leukocytes are subsequently made based on a two-dimensional plot of the florescence measurements.

Other examples of techniques that are classified as being within the flow cytometric approach are shown in Unexamined Published Japanese Patent Public Disclosure No. 20820/1975, H. M. Shapiro et al., J. Histochem. Cytochem., 24 (1), 396-411 (1976); and idem, ibid, 25, (8), 976-989 (1977). According to these methods, a blood sample is stained with 4 volumes of a Dye Solution I, incubated for 3 minutes, further mixed with 20% formaldehyde in a volume equal to the blood, fixed for 5 minutes, and diluted with a diluting Dye Solution II to obtain a concentration 15-20 times as low as the initial value. The so prepared specimen is subjected to measurement with a flow cytometer.

The flow cytometer employed in these methods used either three mercury lamps each of which produces a separate wavelength of light, or three lasers, so as to excite the three fluorescent stains in the dye solutions.

The parameters measured are three kinds of fluorescence, forward scattered light, 90° scattered light and absorbed light. Based on these six parameters, two-dimensional plots are constructed in four stages and analyzed to make leukocyte classification and counting.

In the first version of the method that uses a flow system for leukocyte classification and counting, the disruption of erythrocytes is a prerequisite but depending on a blood sample, it is impossible to effect complete lysis of erythrocytes and the accuracy of measurements may be impaired in such a case.

The examples of the flow cytometric approach that are described in Japanese Patent Publication No. 853/1984 and Blood Cells, 6, 121–140 (1980) are characterized by performing measurements before dye absorption by the cells reaches an equilibrium, or at the time when the difference between the intensities of fluorescence from individual leukocytes attains a maximum during the staining process. However, the time required for attaining an appropriate level of fluorescence intensity in a sample whose leukocyte count is at either one of two extremes will be different from the time for a normal sample and an appropriate staining time must be selected for each samples. As a further problem, this method relies solely on the differential intensity of fluorescences for leukocyte classification and does not necessarily ensure precise separation between different leukocyte types such as lymphocytes and monocytes.

The other examples of the cytometric approach that are described in Unexamined Published Japanese Patent Public Disclosure No. 20820/1975, J. Histochem. Cytochem., 24 (1) 396–411 (1976) and supra, 25 (8) 976–989 (1977) have the disadvantage that they involve many steps of operation, take a prolonged staining time and require the use of reagents in a complex system. Furthermore, practice of these methods requires a very sophisticated and costly apparatus that includes three light sources and which is capable of measuring six parameters. In addition, analysis of such a large number of parameters is inevitably complicated and requires an analyzer of large capacity.

SUMMARY OF THE INVENTION

The present invention has been accomplished in order to solve the aforementioned problems of the prior art techniques for leukocyte classification and counting and it provides a method that enables accurate classification and counting of leukocytes by simple procedures.

The method of the present invention capable of attaining the aforementioned object comprises the following steps:

(a) preparing a specimen for measurement by adding a fresh sample of anti-coagulated blood to a dye solution and allowing it to stand until equilibrium is reached, said dye solution consisting of a buffer for maintaining a pH in the range of 3.5–10.0, an inorganic salt for maintaining the osmolarity of the dye solution at one half to twice the physiological osmolarity so that the leukocytes in the blood will not deform excessively, and a fluorochrome for differentially staining the leukocytes according to their cytochemical characters;

(b) permitting the prepared specimen for measurement to flow through a flow cytometer, differentiating leukocytes from all other corpuscles by the intensity of fluorescence, and measuring the signal of right-angle (rectangular) scattered light and at least one fluorescence signal emitted from the leukocytes; and (c) identifying the type of each of the leukocytes based on the signals emitted therefrom, counting the number of detected leukocytes according to their type, and calculating the proportions of individual leukocyte types.

Of the signals emitted from leukocytes, the right-angle scattering light signal reflects the structual information of an individual cell. The larger the nucleus of a white blood cell and the more granules that are present in it, the greater light reflection will occur in the cell to produce more intense right-angle scattered light. A lymphocyte contains very few or no granules, so the scattered light produced from the lymphocyte is the weakest of all leukocytes. On the other hand, a neutrophil contains many granules and has a large nucleus, so that it produces the intense scattered light. The intensity of scattered light which eosinophils produce is substantially equal to that of scattered light which neutrophils produce. Monocytes, eosinophils and basophils produce scattered light the intensity of which is intermediate between the intensities of scattered light from lymphocytes and neutrophils. For these reasons, the relative intensities of right-angle scattered light emitted from various types of leukocytes are plotted as shown in FIG. 2.

On the other hand, the fluorescence signal reflects the cytochemical characters of leukocytes and depending on the interaction between stains and individual leukocyte types, signals of different intensities are produced from the leukocytes.

Therefore, by combining the right-angle scattered light signal with at least one fluorescence signal depending upon the specific dye used, leukocytes can be classified with a very high resolution.

As will be understood from the foregoing, the method of the present invention has the advantage that no cumbersome operations involving a complicated preliminary treatment are required and that the leukocytes in blood alone can be classified and counted with a flow cytometer after a simple one-step staining procedure has been completed.

DETAILED DESCRIPTION OF THE INVENTION

Figure 1:
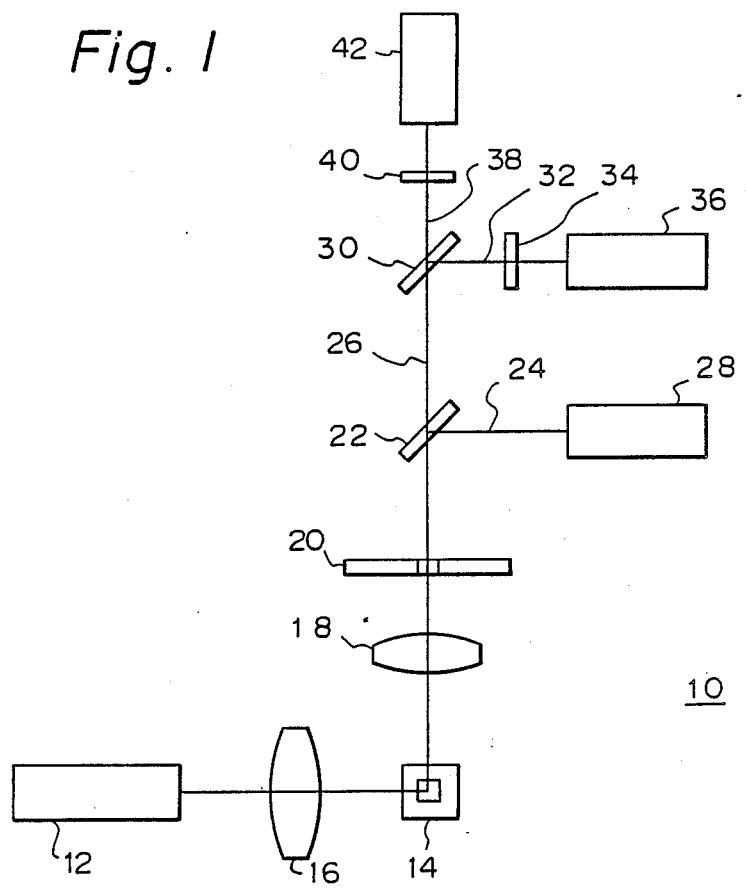
FIG. 1 is a schematic diagram of the optics of a flow cytometer that may be employed in implementing the method of the present invention.
Figure 2:
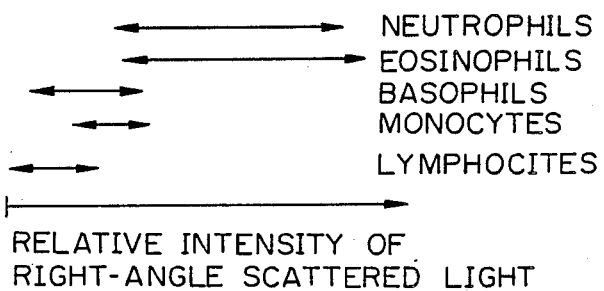
FIG. 2 is a graph showing the relative intensities of right-angle scattered light from five different types of leukocytes.

A specific example of the optics of a flow cytometer employed in the present invention is hereunder described with reference to FIG. 1. The optics shown in FIG. 1 is used in a flow cytometer designed for measuring right-angle scattered light, red fluorescence and green fluorescence. The optics generally indicated by 10 uses an argon ion laser 2 as a light source and it operates at a wavelength of 488 nm, producing an output of 10 mW. Light emitted from the laser 12 is converged by a cylindrical lens 16 and illuminates a blood sample flowing through a flow cell 14.

When the stained leukocytes in the sample are irradiated by the laser light, they produce scattered light and fluorescence. The right-angle scattered light and the fluorescence are converged with a condenser lens 18 and pass through an aperture 20 to fall upon a dichroic mirror 22. The dichroic mirror 22 reflects the right-angle scattered light 24 and transmits the fluorescence 26. The right-angle scattered light 24 reflected from the dichroic mirror 22 is detected in a photomultiplier tube 28. Of the fluorescence 26 that passes through the dichroic mirror 22, red fluorescence 32 is reflected by a interference by erythrocytes is decreased to a level that can be disregarded for practical purposes.

In order to improve the reproducibility of data that can be produced, it is desirable to count no less than about 10,000 white blood cells with a flow cytometer.

The present inventors have found that there are 17 fluorochromes dyes of six groups with which leukocytes can be classified into at least 4 types by flow cytometry with the optics shown in FIG. 1. The names, color index numbers and fluorescence characteristics of these fluorochrome dyes are listed in Table 1 below.

TABLE 1

| Dye Group | Name | C.I. No. | Fluorescence Characteristics | |
|---|---|---|---|---|
| | | | Excitation maximum (nm) | Emission maximum (nm) |
| I. Xanthene dyes | Pyronine Y | 45,005 | 550 | 565 |
| | Rhodamine 3GO | 45,215 | 529 | 552 |
| | Fluorescein | 45,350.1 | 492 | 514 |
| II. Oxacarbocyanine dyes | DiOCl(3)* | — | 480 | 497 |
| | DiOC2(3)* | — | 481 | 498 |
| | DiOC3(3)* | — | 483 | 500 |
| | DiOC5(3)* | — | 485 | 499 |
| | DiOC6(3)* | — | 483 | 499 |
| III. Acridine dyes | Acridine Orange | 46,005 | 493 | 528 |
| | Brilliant Phosphine | 46,035 | 459 | 505 |
| | Rhoduline Orange | 46,005 | 492 / 443 | 530 |
| | Euchrysin 3RX | 46,005 | 441 | 508 |
| | Flavophosphine R | 46,035 | 498 | 525 |
| | Coriphosphine O | 46,020 | 498 | 525 |
| IV. Azine dyes | Neutral Red | 50,040 | 418 | 625 |
| V. Diphenylmethane dyes | Auramine O | 41,000 | 463 | 515 |
| VI. Methine dyes | Astrazon Orange G | 48,035 | 470 | 529 |

*DiOCl(3): 1,1'-dimethyloxacarbocyanine
DiOC2(3): 1,1'diethyloxacarbocyanine
DiOC3(3): 1,1'-di-(n-propyl)-oxacarbocyanine
DiOC5(3): 1,1'-di-(n-pentyl)-oxacarbocyanine
DiOC6(3): 1,1'-di-(n-hexyl)-oxacarbocyanine dichroic mirror 30 and green fluorescence 38 is transmitted through that mirror. The reflected red fluorescence 32 passes through a color filter 34 and is detected in a photomultiplier tube 36. The transmitted green fluorescence 38 passes through a color filter 40 and is detected in a photomultiplier tube 42.

Erythrocytes in the specimen for measurement emit only fluorescence of very low intensity, so if all that is needed is to measure the intensity of fluorescence, erythrocytes will not interfere with the counting of leukocytes even if coincidence of erythrocytes and leukocytes occurs (i.e., erythrocytes and leukocytes pass through the detecting portion simultaneously). However, if one wants to measure the scattered light, erythrocytes which produce scattered light having an intensity comparable to that of the scattered light emitted from leukocytes will interfere with the counting of leukocytes. In this case, one may measure fluorescence and scattered light simultaneously and regard as leukocytes only the corpuscles that emit fluorescence having an intensity greater than a certain level. However, if coincidence of leukocytes and erythrocytes occurs, the scattered light from erythrocytes is superposed on the scattered light from leukocytes, thereby making accurate measurement of scattered light from the leukocytes impossible. In the optics 10 of a flow cytometer shown in FIG. 1, a blood sample is permitted to flow through the flow cell 14 after it has been diluted by, for example, 20 folds so that the probability of coincidence of erythrocytes and leukocytes is reduced and the potential The dyes of these six groups listed in Table 1 have the ability to stain differentially the individual types of leukocytes according to their cytochemical characters. Therefore, if flow cytometry is conducted using one of these dyes with the conditions of staining and measurement and parameters for measurement being appropriately selected, 4-part differentiation of leukocytes can be accomplished as shown in FIGS. 3a to 3d, in which the reference numerals and symbols have the following meanings: 1, lymphocyte; 2, monocyte; 3, neutrophil; 4, eosinophil; 5, basophil; Side Sc., relative intensity of right-angle scattered light; FL., relative intensity of fluorescence; Red. FL., relative intensity of red fluorescence; and Green FL., relative intensity of green fluorescence (the same numerals and symbols used hereinafter have the same meanings).

Figure 3A:
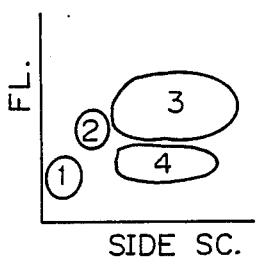
FIG. 3(a) to 3(g) are two-dimensional plots of two signals selected for leukocyte classification.

The dyes of the first and second groups in Table 1 allow leukocytes to be classified into 4 or more types as shown in FIG. 3a, with the intensities of fluorescence and right-angle scattered light being selected as parameters for measurement (see Examples 1 and 2 to be described later in this specification).

Figure 3B:
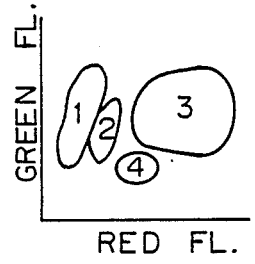

The dyes of the third group allow leukocytes to be classified into 4 or more types as shown in FIG. 3b, with the intensities of green and red fluorescences being selected as parameters for measurement (see Example 3).

Figure 3C:
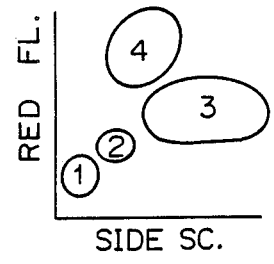

The dye of the fourth group allows leukocytes to be classified into 4 or more types as shown in FIG. 3c, with the intensities of red fluorescence and right-angle scattered light being selected as parameters for measurement (see Example 4).

Figure 3D:
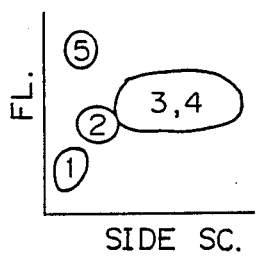

The dyes of the fifth and sixth groups allow leukocytes to be classified into 4 or more types as shown in FIG. 3d, with the intensities of fluorescence and right-angle scattered light being selected as parameters for measurement (see Examples 5 and 6).

Figure 3E:
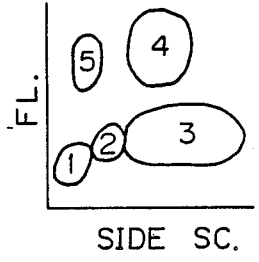

Exemplary conditions for staining and measurement and parameters for measurement that may be employed with the individual dyes listed in Table 1 are summarized in Table 2 below.

group and if fluorescence and right-angle scattered light are used as parameters for measurement, leukocytes can be classified into 5 types as shown in FIG. 3e (see Example 7).

None of the dyes listed in Table 3 is capable of differentiating leukocytes into 4 types or more by light source having a limited wavelength of 488 nm, but differentiation of 3 types (lymphocytes, monocytes and granulocytes) is possible with these dyes. Seven out of the 21 dyes listed in Table 3 are specifically shown in Table 4 and if cytometry is conducted with these dyes under the

TABLE 2

| | | Dye Solution Composition | | | | Wavelength of fluorescence | | Parameters for classification | | |
| --- | --- | --- | --- | --- | --- | --- | --- | --- | --- | --- |
| | | | Dye concentration | NaCl concentration | staining | | | green | red | right-angle scat- |
| Dye | Buffer solution | pH | (μg/ml) | (mM) | time (min) | green (nm) | red (nm) | fluorescence | fluorescence | tered light |
| I. Pyronine Y | 10 mM citrate | 4.5 | 10 | 75 | 4 | | 580- | | O | O |
| Rhodamine 3GO | 10 mM citrate | 4.5 | 30 | 75 | 4 | | 580- | | O | O |
| Fluorescein | 10 mM citrate | 4.5 | 100 | 150 | 8 | 540–600 | | O | | O |
| II. DiOCl(3) | 10 mM citrate | 4.5 | 30 | 75 | 4 | 520–580 | | O | | O |
| DiOC2(3) | 10 mM citrate | 4.5 | 30 | 75 | 4 | 520–580 | | O | | O |
| DiOC3(3) | 10 mM citrate | 4.5 | 30 | 75 | 4 | 520–580 | | O | | O |
| DiOC5(3) | 10 mM citrate | 4.5 | 10 | 150 | 4 | 520–600 | | O | | O |
| DiOC6(3) | 10 mM citrate | 4.5 | 10 | 150 | 4 | 520–580 | | O | | O |
| III. Acridine Orange | 5 mM phosphate | 7.4 | 4 | 150 | 1 | 520–580 | 580- | O | O | |
| Brilliant Phosphine | 10 mM borate | 9.0 | 100 | 150 | 4 | 520–600 | 600- | O | O | |
| Rhoduline Orange | 10 mM borate | 9.0 | 100 | 150 | 4 | 520–580 | 580- | O | O | |
| Euchrysin 3RX | 10 mM borate | 9.0 | 100 | 150 | 4 | 520–580 | 580- | O | O | |
| Flavophosphine R | 10 mM phosphate | 7.0 | 3 | 150 | 4 | 520–580 | 580- | O | O | |
| Coriphosphine O | 10 mM borate | 9.0 | 30 | 150 | 4 | 520–580 | 580- | O | O | |
| IV. Neutral Red | 10 mM phosphate | 7.0 | 30 | 150 | 1 | | 600- | | O | O |
| V. Auramine O | 10 mM borate | 9.0 | 30 | 150 | 4 | | 600- | | O | O |
| VI. Astrazon Orange G | 10 mM borate | 9.0 | 10 | 150 | 4 | 540–600 | | O | | O |

Figure 3F:
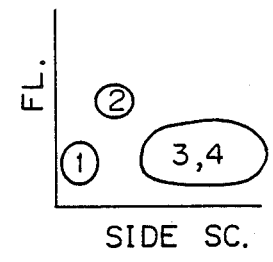

Each of the Acridine Orange and Rhoduline Orange listed in Table 2 is capable of differentiating leukocytes into five types. But the other dyes in Table 2 have to be combined with one another in order to achieve 5-part classification of leukocytes, for instance, if the dye of the fourth group is combined with the dye of the sixth conditions summarized in Table 4 with fluorescence and right-angle scattered light being selected as parameters for measurement, two-dimensional plots can be obtained that produce a very good resolution of lymphocytes, monocytes and granulocytes as shown in FIG. 3f (see Example 8).

TABLE 3

| | | | | Fluorescence characteristics | |
| --- | --- | --- | --- | --- | --- |
| | | Dyes | C.I. No. | Excitation maximum (nm) | Emission maximum (nm) |
| I. Xanthene dyes | | Acridine Red | 45,000 | 530 | 554 |
| | | Rhodamine S | 45,050 | 530 | 551 |
| | | Rhodamine 6G | 45,160 | 530 | 553 |
| | | Rhodamine B | 45,170 | 555 | 585 |
| | | Rhodamine 19 perchlorate | — | 521 | 550 |
| | | Rhodamine 123 | — | 500 | 525 |
| | | Eosin Y | 45,380 | 518 | 540 |
| | | Cyanosine | — | 518 | 540 |
| VII. Oxazine dyes | | Cresyl Fast Violet | — | 585 | 626 |
| | | Darrow Red | — | 495 | 583 |
| VIII. Cyanine dyes | | Acronol Phloxine FFS [DiICl(3)]*3 | — | 540 | 555 |
| | | DiSCl(3)*3 | — | 555 | 570 |
| | | DiSC2(3)*3 | — | 551 | 570 |
| | | 1,1'-diethyl-9-methylthiocarbocyanine bromide [9-Me-DiSC2(3)] | — | 550 | 561 |
| | | 2-[γ-(1'-ethyl-4',5'-benzothiazolylidene)-propenyl]-1-ethyl-4,5-benzoxazolium iodide*2 | — | 517 | 532 |
| IX. Styryl dyes | | Astrazon Red 6B | — | 550 | 590 |
| | | C.I. Basic Violet 16 | — | 550 | 590 |
| | | 2-(DMAS)-1-ethyl-4,5-benzothiazolium | — | 518 | 593 |

TABLE 3-continued

| Dyes | C.I. No. | Fluorescence characteristics | |
|---|---|---|---|
| | | Excitation maximum (nm) | Emission maximum (nm) |
| iodide*1 | | | |
| 2,4-bis(DMAS)-1-ethylpyridinium iodide*1 | — | 470 | 590 |
| 2,6-bis(DMAS)-1-ethylpyridinium iodide*1 | — | 498 | 586 |
| TA-2(Nippon Kankoh-Shikiso Kenkyusho Co., Ltd., Okayama, Japan) | — | 490 | 501 |

*1: DMAS signifies p-dimethylaminostyryl;
*2: abbreviated as NK-720 in Table 4;
*3: DiSCl(3) is 1,1'-dimethylthiocarbocyanine, DiSC2(3) is 1,1'-diethylthiocarbocyan

TABLE 4

| Dyes | Dye Solution Composition | | | Staining time (min) | Fluorescence characteristics | | right-angle scattered light |
|---|---|---|---|---|---|---|---|
| | pH | dye concentration (μg/ml) | NaCl concentration (mM) | | green fluorescence | red fluorescence | |
| Rhodamine S | 9.0 | 30 | 150 | 4 | O | | O |
| Rhodamine 19 perchlorate | 4.5 | 30 | 150 | 1 | O | | O |
| Acronol Phloxine FFS | 4.5 | 3 | 150 | 1 | O | | O |
| 9-Me-DiSC2(3)*3 | 9.0 | 10 | 150 | 1 | | O | O |
| NK-720*2 | 7.0 | 30 | 150 | 1 | O | | O |
| Astrazon Red 6B | 4.5 | 30 | 150 | 4 | | O | O |
| TA-2 | 7.0 | 10 | 150 | 1 | O | | O |

*1: The fluorescence emissions received were green fluorescence (520–580 nm) and red fluorescence (≧580 nm).
*2: For the unabbreviated name of NK-720, see Table 3.
*3: For 9-Me-DiSC2(3), see Table 3.

Figure 3G:
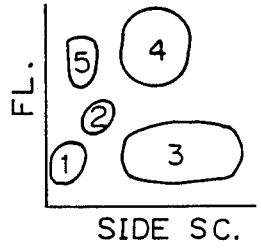

If one or more of the 17 dyes listed in Table 1 are combined with one of the dyes listed in Table 4 and if fluorescence and right-angle scattered light are selected as parameters for measurement, leukocytes can be distinguished in a clearer way as between lymphocytes, monocytes, neutrophils, eosinophils and basophils as shown in FIG. 3g (see Example 9).

In the present invention, not only fluorescence but also right-angle scattered light is used as a parameter for measurement and dyes that have the ability to stain blood cells in a highly differential manner are used either alone or in combination. As a consequence, the present invention accomplished a very efficient differentiation of leukocytes including resolution between lymphocytes and monocytes.

The following examples are given for the purpose of further illustrating the present invention but are in no way intended to limit the scope thereof.

EXAMPLE 1

Figure 4:
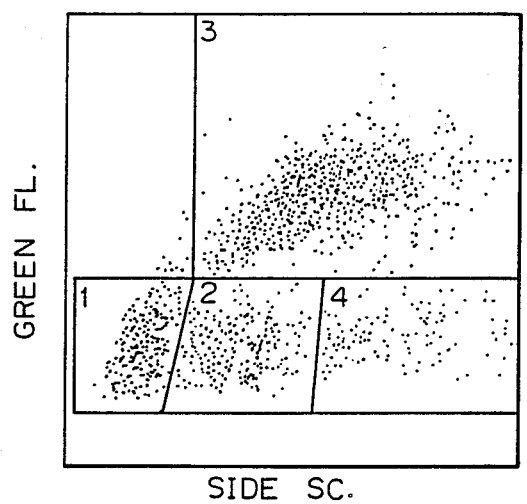
FIGS. 4 to 13 are two-dimensional plots showing the results of leukocyte classification using two selected signals.

Staining with fluorescein in dye group I:
Eighty microliters of EDTA anti-coagulated fresh blood was added to 2 ml of a fluorescein dye solution having the composition shown in Table 2 (i.e., 100 mM citrate buffer solution, pH 4;5; 150 mM NaCl; 100 μg/ml fluorescein) and the mixture was incubated for 8 minutes. The incubated sample was permitted to flow through a flow cell 14 in a flow cytometer having the optics 10 shown in FIG. 1 while being illuminated by laser radiation. A dichroic mirror 30 was of the type that reflected red light having a wavelength of 600 nm and longer, and color filters 34 and 40 were long-pass filters that transmitted wavelengths not shorter than 580 nm and 520 nm, respectively. The sample was caused to flow on the laminar flow principle. The right-scattered light and fluorescence emissions of 520–600 nm were measured only with respect to the white cells that had fluorescence intensities greater than a certain level. The results of analysis are shown in FIG. 4.

EXAMPLES 2–6

Figure 5:
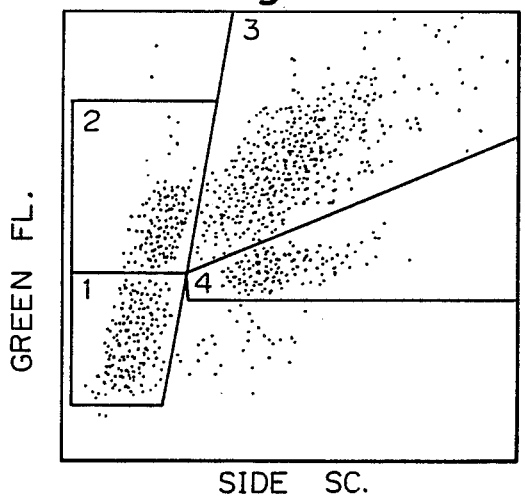
Figure 6:
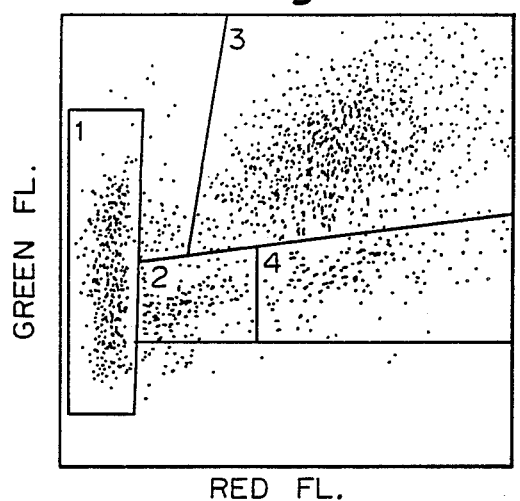
Figure 7:
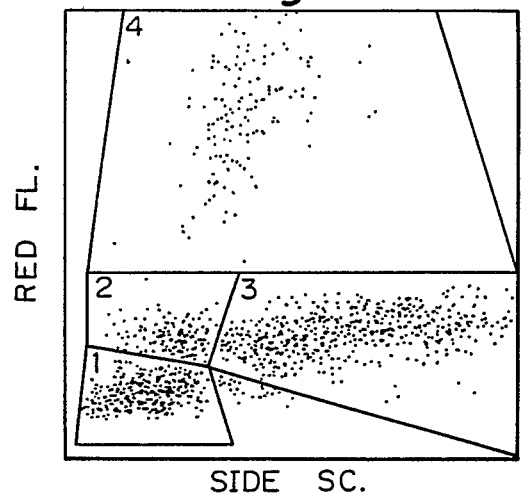
Figure 8:
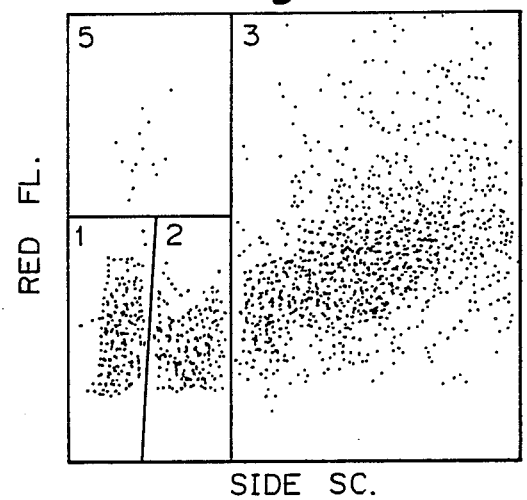
Figure 9:
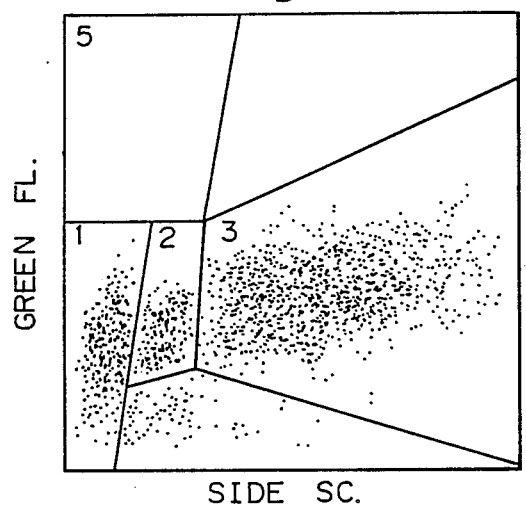

Using dyes of groups II to IV in Table 1, leukocyte measurements were conducted as in Example 1 under the conditions described in Table 2.
Staining with DiOC5(3) of group II ; FIG. 5
Staining with Brilliant Phosphine of group III; FIG. 6
Staining with Neutral Red of group IV ; FIG. 7
Staining with Auramine 0 of group V ; FIG. 8
Staining with Astrazon Orange G of Group VI ; FIG. 9

EXAMPLE 7

Figure 10:
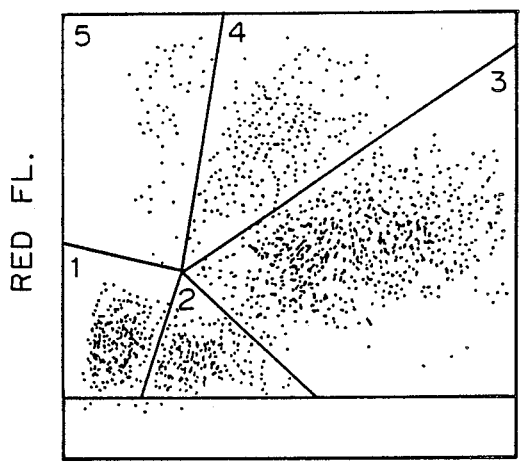

Five-part differentiation of leukocytes by staining with the combination of dyes of groups IV and V in Table 1 (FIG. 10):
Using a dye solution composed of 10 μg/ml of Astrazon Orange G, 1μg/ml of Neutral Red, 75 mM NaCl, and a 10 mM borate buffer solution (pH, 9.0), leukocyte measurement was conducted as in Example 1 except that staining time was 1 minute and that red fluorescence (≧560 nm) and right-angle scattered light were used as parameters for measurement. The results are shown in FIG. 10.

EXAMPLE 8

Figure 11:
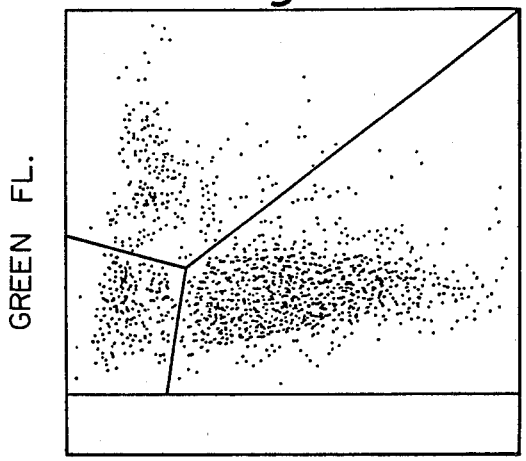

Three-part differentiation of leukocytes by staining with dye in Table 4 (FIG. 11):
Using TA-2, leukocyte measurement was conducted as in Example 1 under the conditions described in Table 4.

EXAMPLE 9

Five part differentiation of leukocytes by staining with the dyes of groups IV and VI in Table 1 as combined with dye in Table 4:

Using a dye solution composed of 10 μg/ml of Astrazon Orange G, 1 μg/ml of Neutral Red, 10 μg/ml of TA-2, 75 mM NaCl, and a 10 mM citrate buffer solution (pH 9.0), leukocyte measurement was conducted as in Example 1 except that the staining time was 1 minute and the parameters for measurement selected were green fluorescence (540–600 nm), red fluorescence ($\geq 600$ nm) and right-angle scattered light.

Figure 12:
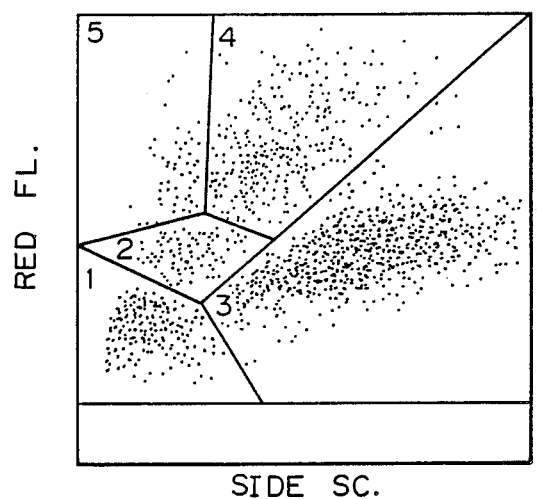
Figure 13:
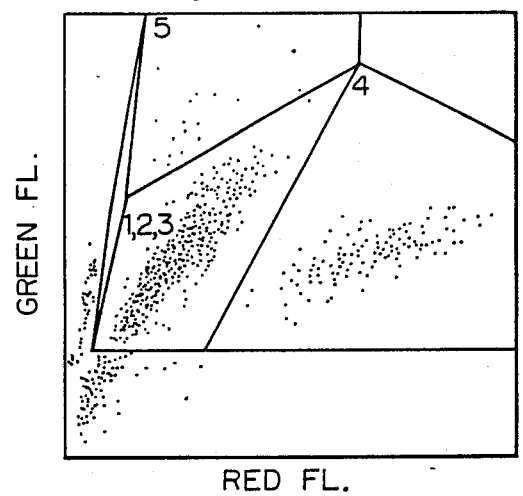
Figure 13:
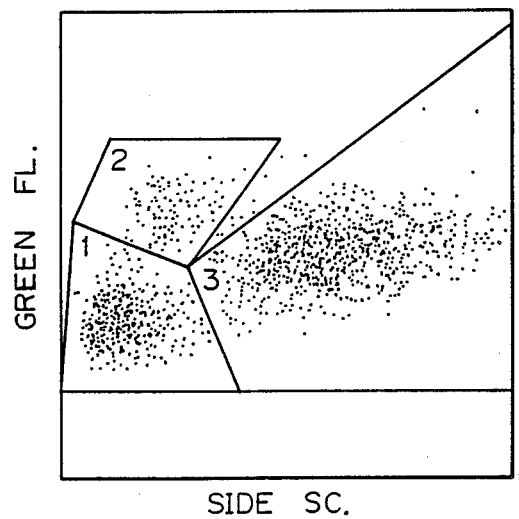

FIG. 12 shows the results of 5-part differentiation of leukocytes based on the intensities of red fluorescence and right-angle scattered light. FIG. 13 shows the results of two-step differentiation that consisted of separation between basophils (5 in FIG. 13a) and eosinophils (4 in FIG. 13a) based on red and green fluorescences, followed by separation between lymphocytes, monocytes and neutrophils (respectively indicated by 1, 2 and 3 in FIG. 13b) based on green fluorescence and right-angle scattered light.

In Examples 1 to 9, all measurements are initiated after the necessary procedures of staining or reaction have been completed (namely, after staining or reaction has reached an equilibrium). Therefore, the sample will not experience any time-dependent change during measurements, and an appropriate level of the intensity of staining or reaction can be attained within a certain period of time no matter how large or small the number of leukocytes in the sample is. This allows for consistent results in measurement and a fluorescence signal of an adequate intensity can be attained even if a light source of a comparatively low output is used. In Examples 1–9 described above, an argon ion laser of 10 mW was employed as a light source in the flow cytometer.

However, the light source in the flow cytometer used in the present invention is not limited to the afore-mentioned argon ion laser of low output and any of the other light sources can be employed, such as a mercury arc lamp, xenon arc lamp, a He-Cd laser, a He-Ne laser and a krypton ion laser, as well as an argon ion laser of high output. If these light sources are used, the conditions of staining, reaction and measurement may be selected as appropriate.

The method of the present invention as applied to classify and count leukocytes in blood has the following advantages.

(1) A sample of measurement can be prepared by a very simple procedure that involves only one-step staining consisting of adding anti-coagulated blood to a dye solution.

(2) The sample can be prepared in approximately one minute and this provides a rapid access time for measurement.

(3) Since measurements are conducted after the necessary procedures of staining have been completed, the sample will not experience any time-dependent change during measurements and an appropriate intensity of staining or reaction can always be attained within a certain period of time irrespective of the nature of the sample (whether it is normal or contains an extremely large or small number of leukocytes). This eliminates the need to change the staining time from sample to sample.

(4) Since measurements are conducted after staining has been completed to provide a high staining intensity, a light source of low output may be employed. In addition, only one light source need be used and two parameters appropriately selected from among two channels of fluorescence and one channel of right-angle scattered light may be measured. Because the number of parameters to be measured and analyzed is this few, the reagent system of the present invention can be used to accomplish flow cytometry of blood with a simple and inexpensive apparatus.

(5) Not only fluorescence but also right-angle scattered light is used as a parameter for measurement, and dyes that have the ability to stain blood cells in a highly differential manner are used either alone or in combination, so leukocytes can be differentiated with a very high resolution between individual types including lymphocytes and monocytes.

(6) Erythrocytes, platelets and immature erythrocytes emit fluorescence that is much weaker than the emission from leukocytes and hence can be clearly distinguished from the latter. This eliminates the need to lyse erythrocytes before measurement.

If the method of the present invention is performed on a blood sample that is diluted to such a level that the probability of coincidence of erythrocytes and leukocytes is adequately reduced, the potential interference by erythrocytes in the measurement of right-angle scattered light can be inhibited to a negligible level.

In accordance with the method of the present invention, accurate and highly reproducible measurements can be achieved by counting no less than 10,000 leukocytes for each sample.

What is claimed is:

1. A method for classifying leukocytes by type, using flow cytometry which comprises the following steps (a) to (c):

(a) preparing a specimen for measuring by mixing a fresh sample of white corpuscle-containing anti-coagulated blood with a dye solution, said dye solution consisting of a buffer for maintaining a pH in a pH range of 3.5–10.0, an inorganic salt for maintaining an osmolarity of the dye solution at one half to twice physiological osmolarity and at least one fluorochrome dye for differentially staining leukocytes according to their cytochemical characters; and allowing the specimen to stand until equilibrium is reached between said fluorochrome dye or fluorochrome dyes of said dye solution and the corpuscles of said mixture;

(b) introducing an aliquot of the specimen, prepared in accordance with step (a), into a flow cell of a flow cytometer, irradiating corpuscles of said aliquot of said specimen in said cytometer with light of a wavelength that excites fluorescence of said fluorochrome dye or fluorochrome dyes of said dye solution, differentiating leukocytes from all other types of corpuscles in said specimen according to intensity of fluorescence from the corpuscles of said aliquot of said specimen, and measuring from the leukocytes of said aliquot relative intensities of right-angle scattered light and at least one fluorescence signal due to said fluorochrome dye or fluorochrome dyes absorbed by said leukocytes from said dye solution; and (c) identifying, according to said relative intensities measured in accordance with step (b), the type of each of said leukocytes of said aliquot, for which relative intensities of right-angle scattered light and fluorescence were measured in accordance with step (b), counting said differentiated leukocytes according to their type, and calculating proportions of individual leukocyte types.

2. A method according to claim 1 for classifying leukocytes into at least four types by using, in the dye solution employed in step (a), one dye, said dye selected from the group consisting of:

| Group I:   | Xanthene dyes        | Pyronine Y<br>Rhodamine 3GO<br>Fluorescein |
|------------|----------------------|--------------------------------------------|
| Group II:  | Oxacarbocynanine dyes | DiOC1(3)<br>DiOC2(3)<br>DiOC3(3)<br>DiOC5(3)<br>DiOC6(3) |
| Group III: | Acridine dyes        | Acridine Orange<br>Brilliant Phosphine<br>Rhoduline Orange<br>Euchrysin 3RX<br>Flavophosphine R<br>Coriphosphine O |
| Group IV:  | Azine dyes           | Neutral Red |
| Group V:   | Diphenylmethane dyes | Auramine O |
| Group VI:  | Methine dyes         | Astrazon Orange G. |

3. A method according to claim 1 for classifying leukocytes into at least three types by using, in the dye solution employed in step (a), one dye, said dye selected from the group consisting of:

| Group I:    | Xanthene dyes | Acridine Red;<br>Rhodamine S;<br>Rhodamine 6G;<br>Rhodamine B;<br>Rhodamine 19 perchlorate;<br>Rhodamine 123;<br>Eosin Y;<br>Cyanosine; |
|-------------|---------------|-----------------------------------------------------------------------------------------------------------------------------------------|
| Group VII:  | Oxazine dyes  | Cresyl Fast Violet;<br>Darrow Red; |
| Group VIII: | Cyanine dyes  | Acronol Phloxine FFS;<br>1,1'-dimethylthio-carbocyanine;<br>1-1'-diethylthio-carbocyanine;<br>1-1'-diethyl-9-methylthiocarbocyanine bromide;<br>2-[γ-(1'ethyl-4',5'-benzothiazolylidene) propenyl]-1-ethyl-4,5-benzoxazolium iodide; |
| Group IX:   | Styryl dyes   | Astrazon Red 6B;<br>C.I. basic Violet 16;<br>2-(p-dimethylaminostyryl)-1-ethyl-4,5-benzo-thiazolium iodide;<br>2,4-bis(p-dimethylamino-styryl)-1-ethyl-pyridinium iodide;<br>2,6,-bis(p-dimethylamino-styryl)-1-ethyl-pyridinum iodide; |

4. A method according to claim 1 for classifying leukocytes into at least five types by using, in the dye solution employed in step (a), at least two dyes, each of said dyes selected from the group consisting of:

| Group I:   | Xanthene dyes         | Pyronine Y<br>Rhodamine 3GO<br>Fluorescein |
|------------|-----------------------|--------------------------------------------|
| Group II:  | Oxacarbocynanine dyes | DiOC1(3)<br>DiOC2(3)<br>DiOC3(3)<br>DiOC5(3)<br>DiOC6(3) |
| Group III: | Acridine dyes         | Acridine Orange |

-continued

| | | Brilliant Phosphine<br>Rhoduline Orange<br>Euchrysin 3RX<br>Flavophosphine R<br>Coriphosphine O |
|---|---|---|
| Group IV: | Azine dyes | Neutral Red |
| Group V:  | Diphenylmethane | Auramine O dyes |
| Group VI: | Methine dyes | Astrazon Orange G. |

5. A method according to claim 4 for classifying leukocytes into at least five types by using, in the dye solution employed in step (a), one additional dye, said additional dye selected from the group consisting of:
Rhodamine S;
Rhodamine 19 perchlorate;
Acronol Phloxine FFS;
2-[γ-(1'-ethyl-4',5'-benzothiazolylidene)propenyl]-1-ethyl-4,5-benzoxazolium iodide;
1,1'-diethyl-9-methylthiocarbocyanine bromide;
Astrazon Red 6B; and 6. A method according to claim 1 wherein the light, with which the corpuscles flowing through the flow cytometer are irradiated in accordance with step (b), is from a light source selected from the group consisting of: an Ar ion laser; a He-Ne laser, a Krypton ion laser; a He-Cd laser; a Hg arc lamp; and a Xe arc lamp.

7. A method according to claim 6 which employs, in the dye solution in step (a), one or more dyes, each of said dyes selected from the group consisting of:
Acridine Red;
Rhodamine S;
Rhodamine 6G;
Rhodamine B;
Rhodamine 19 perchlorate;
Rhodamine 123;
Eosin Y;
Cyanosine;
Cresyl Fast Violet;
Darrow Red;
1,1'-dimethylthiocarbocyanine;
1,1'-diethylthiocarbocyanine;
1,1'-diethyl-9-methylthiocarbocyanine bromide; [9-Me-DiSC2(3)];
2-[γ-(1'-ethyl-4',5'-benzothiazolylidene)propenyl]-1-ethyl-4,5-benzoxazolium iodide;
Astrazon Red 6B;
C.I. Basic Violet 16;
2-(p-dimethylaminostyryl)-1-ethyl-4,5-benzothiazolium iodide;
2-4-bis(p-dimethylaminostyryl)-1-ethyl-pyridinium iodide;
2-6-bis(p-dimethylaminostyryl)-1-ethyl-pyridinium iodide;
Pyronine Y;
Rhodamine 3GO;
Fluorescein;
DiOC1(3);
DiOC2(3);
DiOC3(3);
DiOC5(3);
DiOC6(3);
Acridine Orange;
Brilliant Phosphine;
Rhoduline Orange;
Euchrysin 3RX;
Flavophosphine R;
Coriphosphine O;
Neutral Red;
Auramine O; and
Astrazon Orange G.

* * * * *

UNITED STATES PATENT AND TRADEMARK OFFICE
CERTIFICATE OF CORRECTION

PATENT NO. : 4,933,293

DATED : June 12, 1990

INVENTOR(S) : Tomoyuki Kuroda, et al.

It is certified that error appears in the above-identified patent and that said Letters Patent is hereby corrected as shown below:

On the title page, in the "References Cited", change patent number "3,619,205" (Kleinerman) to --3,916,205--.

On the Face of the Patent, in "References Cited", change patent number "4,492,785" (Hoffman et al.) to --4,492,752--.

Column 2, line 27, delete ".." (period), second occurrence.

Column 2, line 51, change "florescence" to --fluorescence--.

Column 3, line 24, change "samples" to --sample--.

Column 3, line 55, change "equilibrum" to --equilibrium--.

Column 4, line 19, delete ", eosinophils".

Column 4, line 26, change "fIuorescence" to --fluorescence--.

Column 4, line 50, change "FIG." to --FIGS.--.

Column 4, line 64, change "2" to --12--.

Column 5, lines 40-41, change "fIuorescence" to --fluorescence--.

Column 5, line 46, change "fIuorescence" to --fluorescence--.

UNITED STATES PATENT AND TRADEMARK OFFICE
CERTIFICATE OF CORRECTION

PATENT NO. : 4,933,293

DATED : June 12, 1990

INVENTOR(S) : Tomoyuki Kuroda, et al.

It is certified that error appears in the above-identified patent and that said Letters Patent is hereby corrected as shown below:

Column 6, line 7, delete "dyes".

Column 6, line 51, after "Red", delete "." (period).

Columns 7 and 8, Table 2, under "III. Rhoduline Orange", column "Dye concentration", change "100" to --30--.

Columns 9 and 10, Table 3, at the end of the note line identified "*3", change "diethylthiocarbocyan" to --diethylthiocarbocyanine-- and add --, and DiIC1(3) is 1,1',3,3,3',3'-hexamethylindocarbocyanine.--.

Column 9, line 55, before "mM", change "100" to --10--.

Column 9, line 56, change "4;5" to --4.5--.

Column 10, line 46, change "Group" to --group--.

Column 10, line 51, change "IV and V" to --IV and VI--.

Column 10, line 55, after "pH", delete "," (comma) (first occurrence).

Column 11, line 6, change "citrate" to --borate--.

Column 12, line 2, change "fIuorescence" to --fluorescence--.

Column 13, line 11, change "Oxacarbocynanine" to --Oxacarbocyanine--.

Column 13, line 53, change "2,6," to --2,6--.

UNITED STATES PATENT AND TRADEMARK OFFICE
CERTIFICATE OF CORRECTION

PATENT NO. : 4,933,293
DATED : June 12, 1990
INVENTOR(S) : Tomoyuki Kuroda, et al.

It is certified that error appears in the above-identified patent and that said Letters Patent is hereby corrected as shown below:

Column 13, line 54, after "iodide", change ";" (semicolon) to --.-- (period).

Column 13, line 64, change "Oxacarbocynanine" to --Oxacarbocyanine--.

Column 14, line 20, change "; and" to --.-- (period).

Column 14, line 38, after "Darrow Red;", insert as new line --Acronol Phloxine--.

Column 14, line 48, change "2-4" to --2,4--.

Column 14, line 50, change "2-6" to --2,6--.

Signed and Sealed this

Thirtieth Day of June, 1992

Attest:

DOUGLAS B. COMER

*Attesting Officer*  *Acting Commissioner of Patents and Trademarks*